United States Patent [19]

Green et al.

[11] 4,304,910

[45] * Dec. 8, 1981

[54] QUARNARY AMMONIUM POLYMERIC ANTI-MICROBIAL AGENT

[75] Inventors: Harold A. Green, Havertown, Pa.; John J. Merianos, Jersey City; Alfonso N. Petrocci, Glen Rock, both of N.J.

[73] Assignee: Kewanee Industries, Inc., New York, N.Y.

[ * ] Notice: The portion of the term of this patent subsequent to May 16, 1995, has been disclaimed.

[21] Appl. No.: 29,778

[22] Filed: Apr. 13, 1979

Related U.S. Application Data

[63] Continuation-in-part of Ser. No. 902,894, May 4, 1978, Pat. No. 4,190,644, which is a continuation-in-part of Ser. No. 744,617, Nov. 24, 1976, Pat. No. 4,089,977.

[51] Int. Cl.$^3$ .................. C07D 401/14; C07D 401/06; C07D 413/14; C07D 413/06
[52] U.S. Cl. ..................... 544/87; 546/186; 546/187; 260/239 B; 260/326.5 R; 564/292
[58] Field of Search ............... 544/87; 260/567.6 H, 260/567.6 P, 326.5 R; 564/292, 186, 187, 239 B

[56] References Cited

U.S. PATENT DOCUMENTS

| | | | |
|---|---|---|---|
| 2,933,529 | 4/1960 | Hwa | 544/87 |
| 2,941,004 | 6/1960 | Pinson et al. | 544/87 |
| 3,725,312 | 4/1973 | Panzer et al. | 260/567.6 P |
| 3,738,495 | 6/1973 | Panzer et al. | 260/567.6 P |
| 4,027,009 | 5/1977 | Grier et al. | 424/78 |
| 4,089,977 | 5/1978 | Green et al. | 424/329 |
| 4,111,679 | 9/1978 | Shair | 424/329 |
| 4,196,217 | 4/1980 | Rancurel | 564/292 |
| 4,250,112 | 2/1981 | Löbach | 564/292 |

*Primary Examiner*—Mark L. Berch
*Attorney, Agent, or Firm*—Arthur A. Jacobs

[57] ABSTRACT

A method for synthesizing compounds of formula:

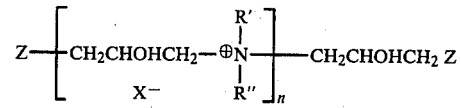

in which R' and R'' (I) are the same or different monovalent branched or unbranched alkyl groups of from 1 to 18 carbon atoms, optionally substituted by from 1 to 2 hydroxyl groups, the sum of the carbon atoms in R' and R'' being at least three; or (II) form a 5, 6, or seven membered ring when taken together with N; or (III) form the N-Morpholino group when taken together with N and Oxygen, wherein Z represents either X or —N R'R'', wherein X is a halogen of atomic weight above 30, and wherein n represents an integer of from 2 to 20.

10 Claims, No Drawings

QUARNARY AMMONIUM POLYMERIC ANTI-MICROBIAL AGENT

This application is a continuation-in-part of Ser. No. 902,894 filed May 4, 1978 now issued as U.S. Pat. No. 4,190,644, dated Feb. 26, 1980, which in turn is a continuation-in-part of Ser. No. 744,617, filed Nov. 24, 1976 and which is now issued as U.S. Pat. No. 4,089,977 dated May 16, 1978. The disclosures of these applications are incorporated by reference into this application.

In the aforesaid applications it was disclosed that compounds, or mixtures of compounds of formula

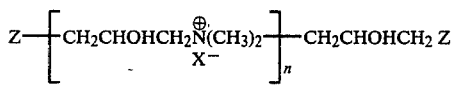

in which Z represents X or the dimethylamino group, X is a halogen atom whose atomic weight is greater than 30, and wherein n is an integer of from 2 to 20, are non-foaming anti-microbial agents. It was also disclosed that, compounds of such a formula or mixtures of such compounds, are good hair conditioners because they are substantive to hair, are sufficiently water soluble even in the presence of relatively high concentrations of anionic and other cleansing and lathering surfactants, do not flake off hair because they do not build up excessively on the hair even after sustained use, impart a smooth feeling to hair, permit combing without excessive "drag", and can be readily formulated into shampoos and creme rinses.

Another unique use of the above compounds that was disclosed is for flocculation in aqueous systems. As flocculants they cause sedimentation of some materials which might otherwise remain in aqueous suspension.

It has now been found that the family of polymeric quaternary compounds shown by the formula above, but in which the two methyl groups that are bonded to the nitrogen in the formula are replaced by other groups, also have anti-bacterial, hair-care, and flocculation properties which are almost identical to these respective properties found in the dimethyl compounds. The properties of the polymers of this invention do differ from the properties of the previously disclosed polymers, but primarily in degree.

The only apparently difference between the compounds of this invention and the aforementioned disclosed compounds, is that the present compounds are not non-foamers.

More specifically, it has been found that compounds generally, of the formula:

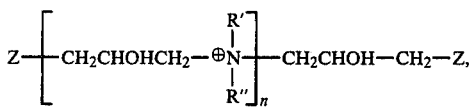

in which R' and R" (I) are the same or different monovalent branched or unbranched alkyl groups of from 1 to 18 carbon atoms, optionally substituted by from 1 to 2 hydroxyl groups, the sum of the carbon atoms on R' and R" being at least 3; or (II) form a 5, 6, or 7 membered ring when taken together with N; or (III) form the N-morpholino group when taken together with N and oxygen, and wherein Z represents either X or —N R'R", wherein X is a halogen of atomic weight above 30, and wherein n represents an integer of from 2 to 20, have anti-microbial properties, have good hair-care properties because they impart a smooth feeling to the hair, but do not build up on the hair after sustained use, and that they permit combing of the hair without excessive "drag". In addition they act as flocculants in aqueous systems because they cause sedimentation of particles which might otherwise remain in suspension.

The method of testing these compounds for anti-microbial activity is described in U.S. Pat. No. 4,089,977; and the methods for hair care and flocculant testing is described in application Ser. No. 902,894, now U.S. Pat. No. 4,190,644.

The syntheses of preferred embodiments of these compounds are described in the examples below as follows:

EXAMPLE 1

One mole of 1,3 dichloro-2-propanol (129 grams) and 10 moles of the secondary amine $(C_2H_5)_2NH$ (about 730 grams) were mixed with about one liter of a 1:1 water-/isopropanol mixture and heated in a autoclave for about 2 hours at about 80°–90° C., after which time analysis for ionic chloride showed that the reaction was virtually complete (5.90% found; 5.92% calculated).

The reaction mixture was treated with about 300 grams of 50% aqueous NaOH, and the unreacted amine was recovered. The top layer of the separated mixture weighed about 220 grams and, when distilled at atmospheric pressure at 185°–200° C., yielded about 185 grams of 1,3-bis-diethylamino-2-propanol (about 92% of theory).

EXAMPLE 2

The synthesis described in Example 1 was repeated, except that water alone was used as the solvent. The yield was about 88% of theory.

EXAMPLE 3

The synthesis of Example 1 was repeated, except that isopropanol alone was used as the solvent. The yield was about 92% of theory.

EXAMPLE 4

The procedures described in Examples 1, 2 and 3 were repeated except that the following 2° amines replaced diethyl amine: diisopropyl amine, dibutyl amine, dioctyl amine, dodecyl methyl amine, diethanol amine, pyrrolidine, and morpholine.

EXAMPLE 5

202 grams of 1,3-bis-diethylamino-2-propanol (1 mole), the compound synthesized in any one of Examples 1, 2 and 3, 129 grams of 1,3-dichloro-2-propanol (1 mole) and about 400 ml. of 1:1 water/isopropanol mixture, by volume, were heated with stirring at about 40° C., for 10 hours, after which analysis for ionic chloride showed that the reaction was at least 97% complete. The product was stripped of volatile material in vacuo until the liquid residue contained about 50% active material.

Analysis of the product for both total chlorine and ionic chloride indicated that a small fraction of the polymeric chains had either one or two non-ionic chlorine termini. Repeated analyses after repeated syntheses indicated that about 0.01 to about 0.05 mole of non-ionic chlorine was present in the final product, either at one terminal or at both termini of the chain. Therefore, a true representation of the product would be as follows:

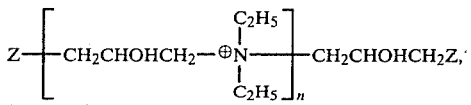

where Z may be either —Cl or —N($C_2H_5$)$_2$, with the overwhelming product being that in which Z is —N($C_2H_5$)$_2$ The number of chlorine termini in the chain could be reduced to practically nothing by starting with a molar excess of about 5%–10% of 1,3-bis-diethylamino-2-propanol, or by heating the product of the equimolar reaction with a little diamine. However, the product made by using an equimolar ratio of reactants, the product made by heating the polymer with a little diamine, and the product made by using a little excess of diamine as reactant, all displayed approximately identical antimicrobial, hair-care and flocculant properties, despite small differences in the quantity of organically bound chlorine.

EXAMPLE 6

The procedure of Example 5 was repeated, using as reactants the diamines made in Example 4. The ratio of water/isopropanol was varied between about 1:3 and 3:1 but there appeared to be no difference in the properties of the products due to different solvent mixture ratios.

The temperature and reaction times were also varied, it being found that the higher the temperature, the lower the reaction time. For example, at about 90° C., in 1:1 water/isopropanol mixture as solvent, the reaction was completed in an average time of about 2 hours, whereas to 50° C., the average time was about 9 hours.

No effort was made to determine the optimum conditions for optimum yields with regard to temperature, time, or concentration of reactants or solvent because the yields were so high in all cases.

No effort was made to determine the exact range of molecular weights of the polymeric product, but viscosity observations led to the estimate that at least 50% of the product was that in which n equals from 2 to 5.

The invention claimed is:

1. A compound or mixture of compounds formed by the reaction between R'R''NCH$_2$CHOHCH$_2$NR'R'' and an approximately equimolar quantity of 1,3-dihalo-2-propanol at a temperature of between about 40° C. and about 95° C. for between about 2 to about 12 hours, R' and R'' being either (I) the same or different monovalent, branched or unbranched alkyl groups of from 1 to 18 carbon atoms either unsubstituted or substituted by either 1 or 2 hydroxyl groups, the sum of the carbon atoms in R' and R'' being at least 3, or (II) form a 5, 6 or 7 membered monoheterocyclic saturated ring when taken together with N, the hetero atom being nitrogen or (III) when taken together with nitrogen and oxygen form the N-morpholino group.

2. The product of claim 1 in which at least 50% by weight of the mixture of products are compounds in which n is between 2 and 5.

3. The product of claim 1 in which

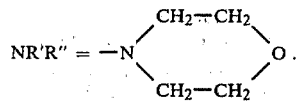

4. The product of claim 1 in which R'=R''=$C_2H_5$.
5. The product of claim 1 in which R'=R''=—CH(CH$_3$)$_2$.
6. The product of claim 1 in which R'=R''=—CH$_2$CH$_2$OH.
7. The product of claim 1 in which R'=R''=—C$_4$H$_9$.
8. The product of claim 1 in which R'=R''=—C$_8$H$_{17}$.
9. The product of claim 1 in which R'=—CH$_3$ and R''=—C$_{12}$H$_{25}$.
10. The product of claim 1 in which

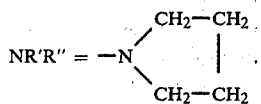

* * * * *